(12) United States Patent
Koike et al.

(10) Patent No.: US 6,342,064 B1
(45) Date of Patent: *Jan. 29, 2002

(54) CLOSURE DEVICE FOR TRANSCATHETER OPERATION AND CATHETER ASSEMBLY THEREFOR

(75) Inventors: Kazuyuki Koike, deceased, late of Suginami-ku, by Noriko Koike, Kanako Koike, Yusuke Koike, legal representatives; Toshiki Kobayashi, Kawagoe; Yoshikazu Kishigami; Katsuya Miyagawa, both of Osaka, all of (JP)

(73) Assignee: Nipro Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/469,320

(22) Filed: Dec. 22, 1999

(30) Foreign Application Priority Data

Dec. 22, 1998 (JP) .............................. 10-363870

(51) Int. Cl.⁷ .............................................. A61B 17/08
(52) U.S. Cl. ...................................... 606/213; 606/151
(58) Field of Search ................................. 606/213, 151, 606/138, 157–158, 215–216, 220, 232; 604/523, 164.01; 623/11

(56) References Cited

U.S. PATENT DOCUMENTS

| 4,917,089 A | * | 4/1990 | Sideris ....................... 606/213 |
| 5,108,420 A | * | 4/1992 | Marks ........................ 606/213 |
| 5,284,488 A | * | 2/1994 | Sideris ....................... 606/213 |
| 5,433,727 A | * | 7/1995 | Sideris ....................... 606/215 |
| 5,507,811 A | * | 4/1996 | Koike et al. ................. 606/151 |
| 5,593,422 A | * | 1/1997 | Mujis Van de Moer .... 606/213 |
| 5,741,297 A | * | 4/1998 | Simon ........................ 606/213 |
| 6,080,182 A | * | 6/2000 | Shaw ......................... 606/213 |
| 6,106,532 A | * | 8/2000 | Koike et al. ................ 606/138 |

* cited by examiner

Primary Examiner—Kennedy Schaetzle
Assistant Examiner—Kriste Droesch

(57) ABSTRACT

An easily foldable closure device for transcatheter operations, comprises: a flat closure member including a closure membrane and a frame for fimbriating a periphery of the membrane; a fixing member for fixing the closure member to a tissue surrounding a defect aperture; and a connecting member fixed at one end to the fixing member and at the other end to the closure member for holding them in close proximity to one another. The frame, fixing member and connecting member are respectively made of the same or different shape-memory alloys with a shape recovery temperature of 30 to 37° C.

7 Claims, 7 Drawing Sheets

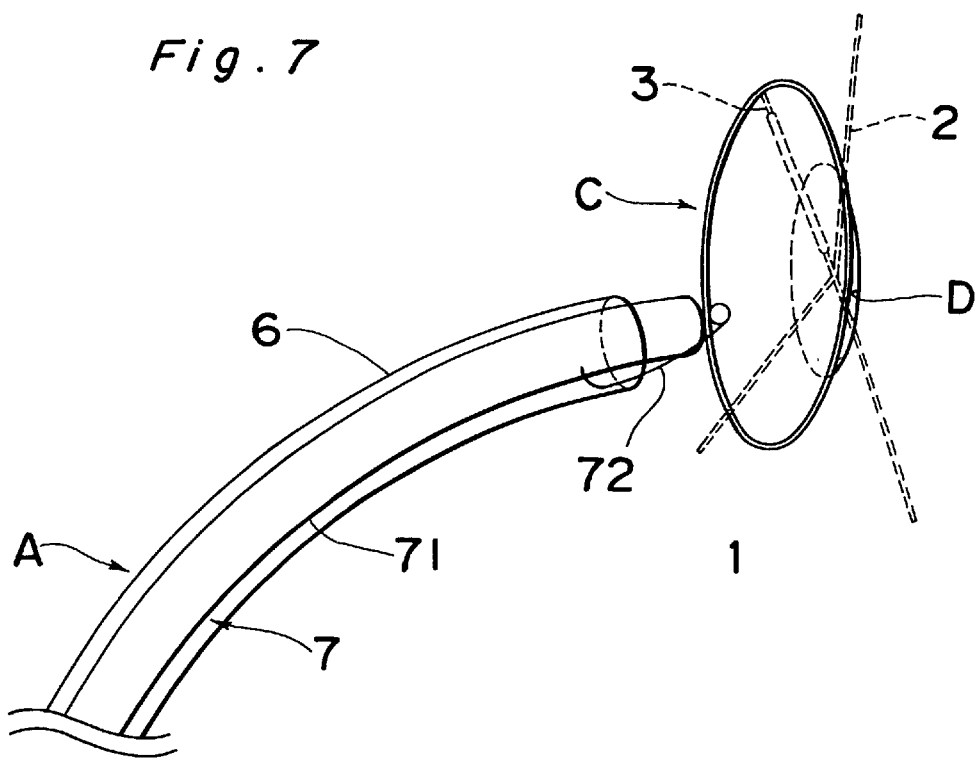
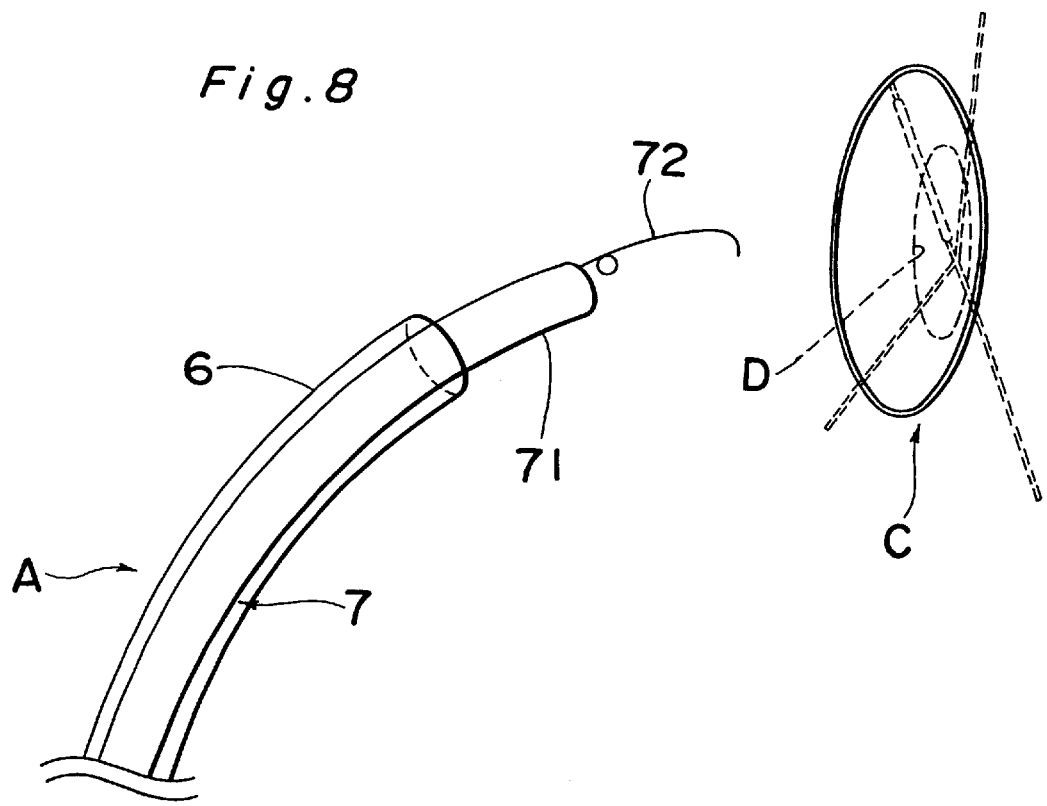

CLOSURE DEVICE FOR TRANSCATHETER OPERATION AND CATHETER ASSEMBLY THEREFOR

BACKGROUND OF THE INVENTION

The present invention relates to a closure device and a catheter assembly suitable for transcatheter operations, i.e., operations for closing or repairing endocardiac or vascular defects.

At present, the Fontan operations have been performed as the repair operations of complex cardiac anomalies such as a single ventricle. In this operation, the cardiac function is repaired by employing a single ventricle for the systemic circulation system, and by directly leading the blood from the vein of the systemic circulation system to the pulmonary artery in the pulmonary circulation system. After this operation, however, extreme decrease in cardiac output may occur because of transient ventricular hypofunction or increase in pulmonary vascular resistance, associated with vasospasm or residual peripheral pulmonary arteriostenosis. Thus, it occasionally becomes difficult to perform postperative management.

In order to avoid increase of the pulmonary vascular resistance and decrease of the cardiac output, therefore, it is general practice for the operation to form a small fenestration or perforation of about 4 mm between atria (in most cases, the interatrial septum is made of an artificial membrane) to allow the blood to flow through the small fenestration or perforation. This procedure followed by formation of the small fenestration or perforation is referred to as the Fontan fenestration. The surgical operation is generally carried out as a method of treatment for closing the small fenestration after the Fontan fenestration. As a matter of course, however, this surgical operation is followed by thoracotomy of a patient in addition to the treatment of the affected area, which imposes a burden on the patient. In particular, in case of child patients, this burden is considerably large.

Percutaneous transluminal therapeutic catheterization is known as a noninvasive procedure for repairing endocardial defects. In this procedure, an atrial septal defect is closed by transveneously inserting an intercardiac catheter into the heart, and closing the atrial septal defect with an occlusion device. The first clinical success of this method was reported by King and Mill in 1976. In the method carried out by King et al, closure of the atrial-septal defect is carried out by introducing left and right atrial double umbrellas into an atrium with an insertion tool composed of a core wire and a double-layered catheter coaxially arranged thereon, fitting the umbrellas on the interatrial septum so that the interatrial septum is sandwiched between them, and then combining the umbrellas into one.

However, this method can not be applied to children, especially, to preschool children since it uses a very thick insertion tool and hard umbrellas. To solve this problem, Rashkind investigated miniaturization of the device, developed in 1977 a single umbrella type occlusion plug with hooks, and reported its clinical success in children. However, this procedure has another problem such that the plug may be occasionally caught in an unintended site of the heart because of its hooks. Thus, when once the umbrella was opened in the heart, the umbrella-like member can not be changed in its position or withdrawn from the site, resulting in emergency operation. To overcome such disadvantages, Rashkind further developed an improved occlusion plug comprising two umbrellas united with one another. This plug has widely been put into clinical use for closure of patent ductus arteriosus.

On the other hand, Lock et al developed a clamshell-shaped intraatrial occlusion device and applied for a patent (JP-A 5-237128), which has been modified by additionally providing coil springs for the double umbrella occlusion plug of Rashkind so that a thin interatrial septum is firmly sandwiched between two umbrellas under the action of the coil springs arranged at each middle portion of eight stainless steel frames of the plug.

This occlusion device is so designed as to be firmly fitted on the thin interatrial septum when the two umbrellas members are in close contact with one another under the overlapped conditions. Because of its configuration similar to a clamshell of a bivalve, this device is called a "clamshell septal occluder". In use, the treatment is carried out by introducing an elongated sheath of 11 French thick into the repair site through a femoral vein of a patient. Since this method is applicable to a patient with a weight of more than 8 kg, it has been widely used as a percutaneous transluminal therapeutic transcatheter closure of atrial septal defects.

The closure treatment of the small hole after Fontan fenestration is done with the occlusion plug by percutaneous transluminal therapeutic transcatheterization.

However, in the method of closing the small hole caused by the Fontan fenestration with the occlusion plug of the prior art, adhesion of thrombus may occur because of a large occlusion plate of the plug, resulting in high risk of complications.

Further, if disembarrassment or dislodgement of the occlusion device has taken place, it is difficult to withdraw the occlusion plug because of its shape or size.

The present invention has been made in view of the above-mentioned circumstances and aimed at providing a closure device for transcatheter operations, that is simple in shape, easy to operate, capable of closing a small hole safely and infallibly, easy to withdraw and less likely to cause adhesion of a thrombus. Also, the present invention is aimed at providing a catheter assembly for introducing the closure device into the site of operation.

SUMMARY OF INVENTION

As the result of assiduous studies for solution of the above problem, the present inventors have conceived an idea of providing a closure membrane with a fixing means of fixing the closure membrane to a tissue wall surrounding a defect aperture, said fixing means exhibiting a shape memory behavior and recovering its memorized shape when heated to the body temperature to sandwich the tissue wall from both sides of the defect aperture between the fixing means and the closure membrane.

In other words, the subject matter of the present invention is directed to an easily foldable closure device for transcatheter operations, comprising: a flat closure member including a closure membrane and a frame for fimbriating a periphery of the membrane; a fixing member for fixing the closure member to a tissue surrounding a defect aperture; and a connecting member fixed at one end to the fixing member and at the other end to the closure member for holding them in close proximity to one another. The frame, fixing member and connecting member are respectively made of the same or different shape-memory alloys with a shape recovery temperature of 30 to 37° C.

According to the present invention, there is provided a closure device for transcatheter operations, comprising: a flat closure member including a closure membrane made of a fabric or non-woven fabric of a bio-compatible material, and a fringing frame for fimbriating or bordering a periphery of said closure membrane, said fringing frame being made of a shape-memory alloy with a shape recovery temperature of 30 to 37° C.; a fixing member for fixing said closure member to a tissue surrounding a defect aperture, said fixing member being approximately parallel to one plane of said closure member and adapted to be located on one side of said defect aperture so that said tissue is sandwiched between said fixing member and said closure member located on the opposite side of said defect aperture, said fixing member being made of a shape-memory alloy with a shape recovery temperature of 30 to 37° C.; and a connecting member fixed at one end to said fixing member and at the other end to the above-mentioned closure member for holding said closure member and fixing member in close proximity to one another, said connecting member being made of a shape-memory alloy with a shape recovery temperature of 30 to 37° C., said closure device being easily foldable at a temperature lower than the shape recovery temperature of said shape memory alloys.

In an embodiment of the present invention, the fringing frame, the fixing member and the connecting member may be formed in one united body. In this case, it is preferred to cover a joint portion of the connecting member and the fringing frame with a tubular covering member to prevent the fixing member from reversing its course.

Further, a base of the fixing member may be stitched to the closure membrane of the closure member with a thread so that the defect aperture is located in the central portion of the closure member when the defect aperture is closed.

In addition, the closure member may be provided with a grappling hole to make it easy to hold the closure device by the holding means of the catheter assembly.

According to the invention, there is also provided a catheter assembly for use in combination with the occlusion device refined as above, comprising a sheath opened at both ends and being able to accommodate a folded closure device, of an operating rod provided at a distal end thereof with a holding means for releasably holding said closure device is provided. The said operating rod is being insertable into sheath from one end thereof under conditions of holding said closure device and being able to unsheathe said closure device through the opposite end of said sheath.

In an embodiment of the present invention, it is preferred to constitute the holding means with an easily flexible linear member extending from the distal end of the operating rod in the axial direction thereof.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 7 is an illustration of a percutaneous closure treatment employing the closure device and catheter assembly of the present invention;

FIG. 8 is an illustration of a percutaneous closure treatment employing the closure device and catheter assembly of the present invention.

DETAILED DESCRIPTION OF THE PREFERRED EMBODIMENTS

The embodiment of the present invention will be explained below on the basis of the accompanying drawings.

Firstly, the explanation will be made of the closure device [C] for transcatheter operations of the present invention.

Figure 1:
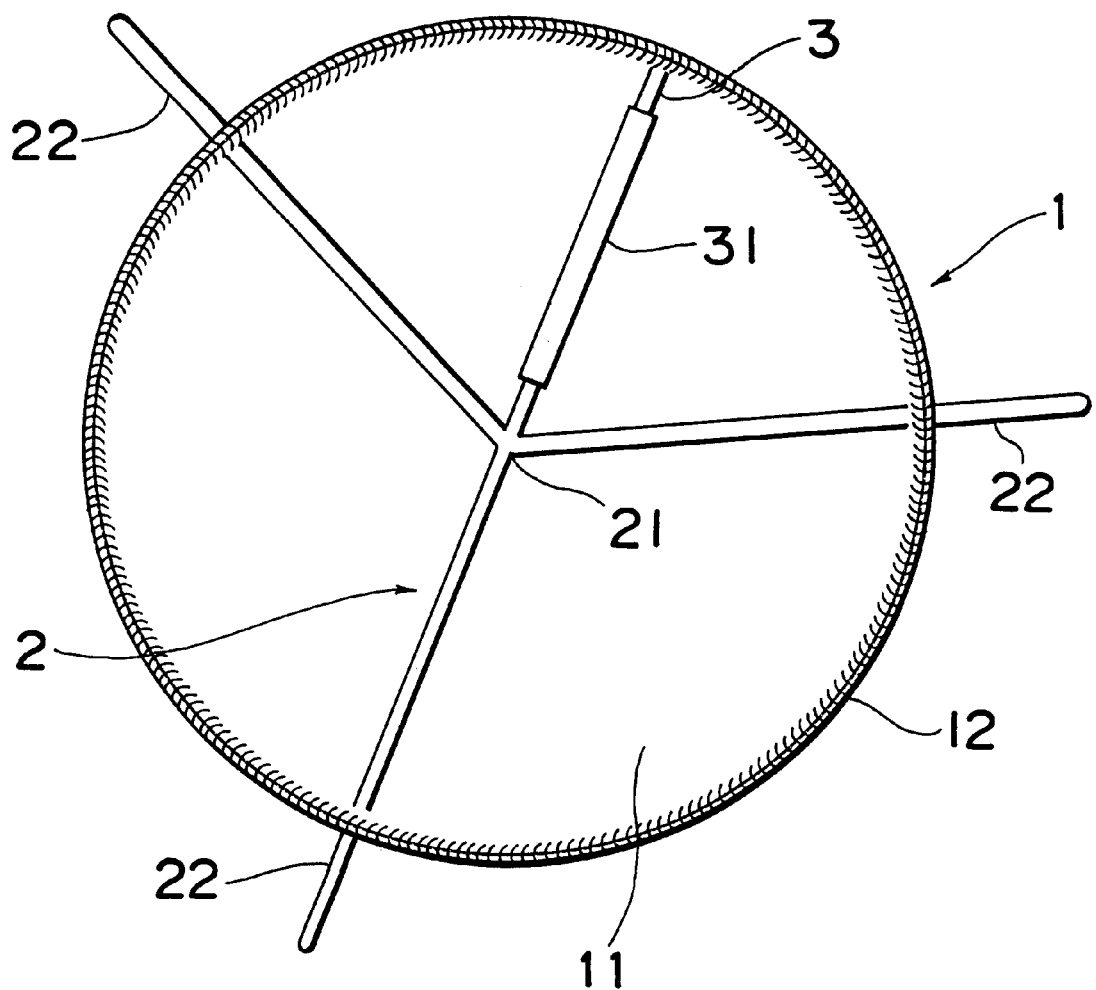
FIG. 1 is a plan view illustrating one embodiment of a closure device of the present invention.
Figure 2:
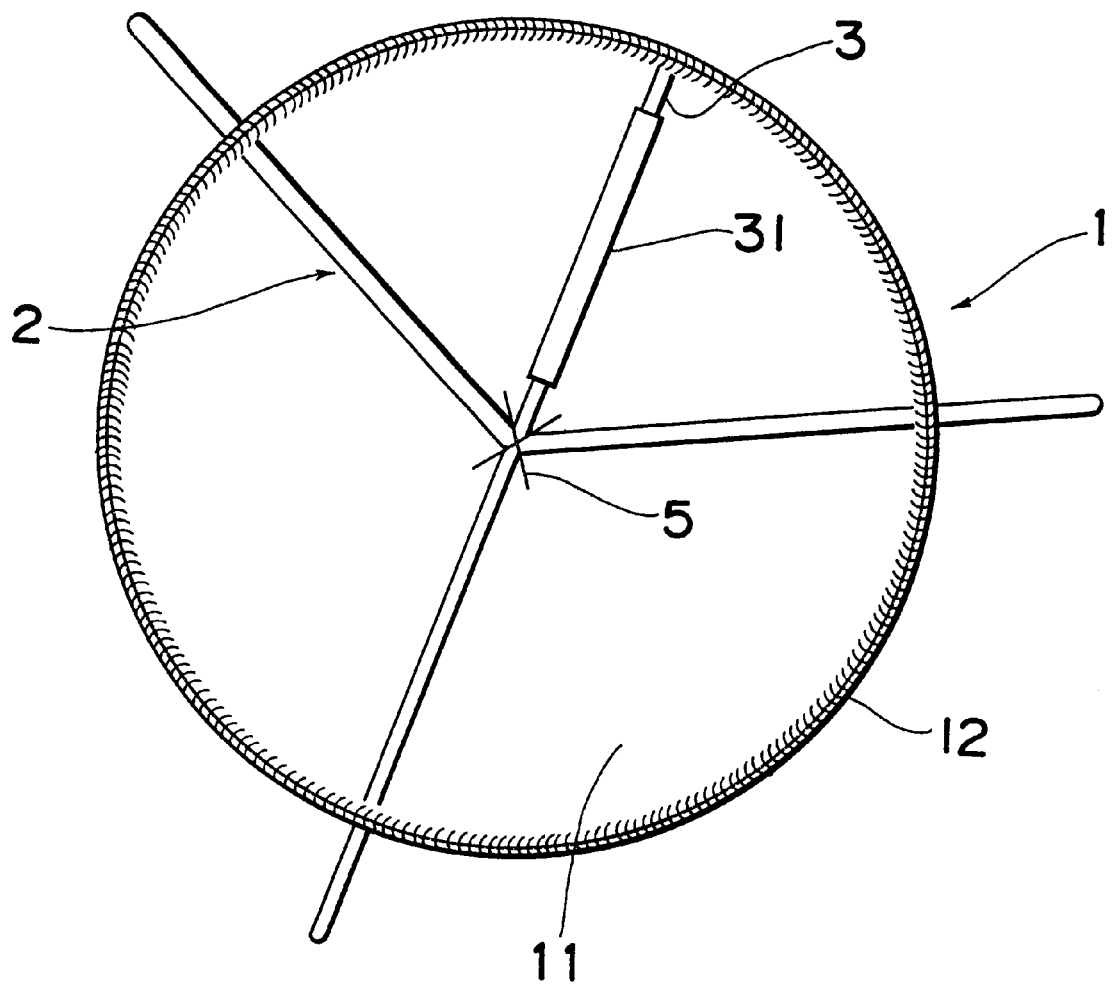
FIG. 2 is a plan view illustrating another embodiment of the closure device of the present invention.
Figure 3:
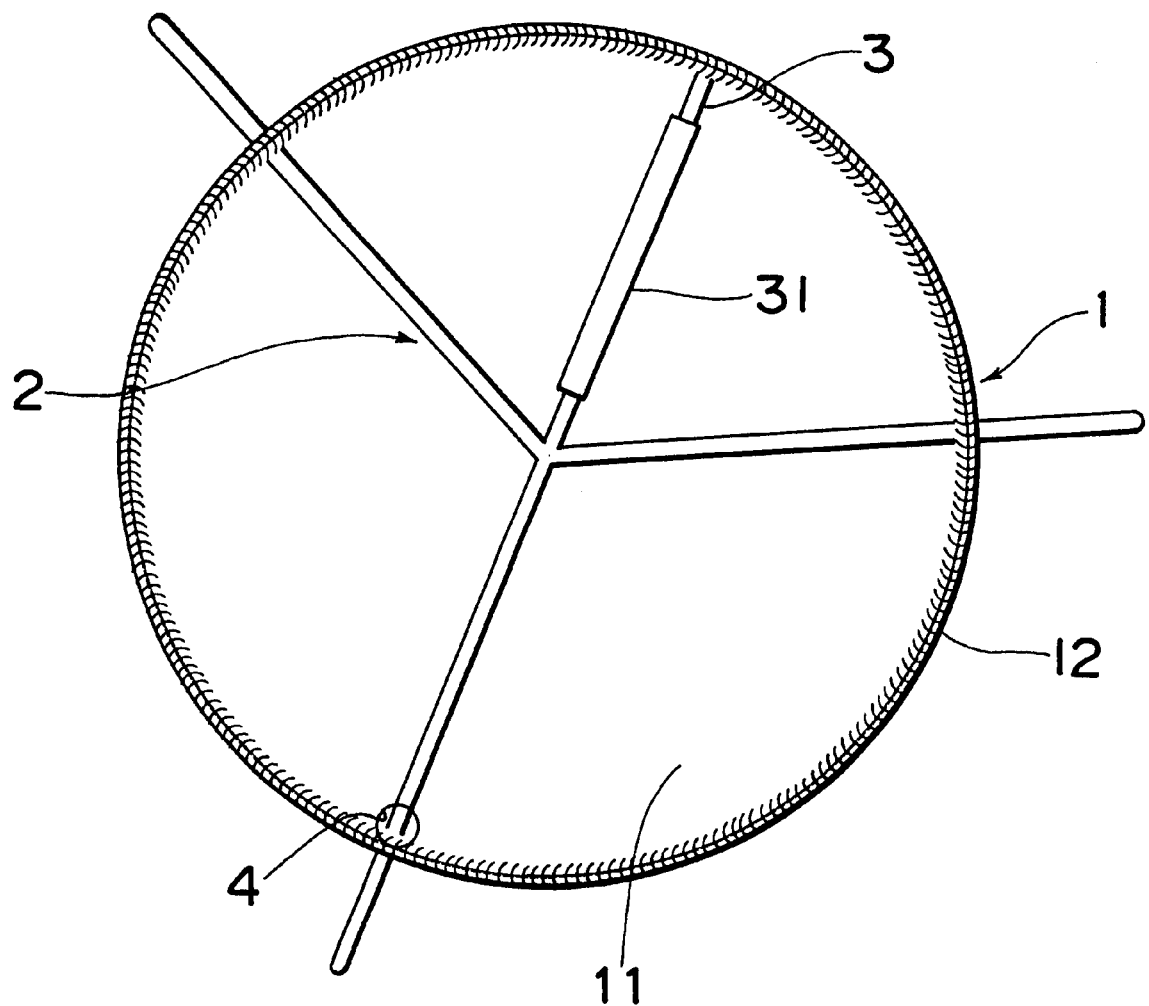
FIG. 3 is a plan view illustrating still another embodiment of the closure device of the present invention.

As shown in FIGS. 1 to 3, the closure device C of the present invention comprises an easily foldable closure member 1, a fixing member 2 for fixing the closure member 1 to a tissue surrounding a defect aperture, and a connecting member 3 for holding the closure member 1 and the fixing member 2 in close proximity of one another. The connecting member 3 is fixed at one end to the fixing member 2 and at the other end to the closure member 1.

Preferably, the closure member 1 is composed of a closure membrane 11 made of a bio-compatible material and a fringing frame 12 made of a shape-memory alloy with a shape recovery temperature of 30 to 37° C. for fimbriating or bordering a peripheral portion of the closure membrane 11. The closure member 1, the fixing member 2 and the connecting member 3 may be formed as one united body. Also, the closure membrane 11 of the closure member 1 may be fixed to the base 21 of the fixing member 2 with a thread 5 passing through the central portion of the closure membrane 11 of the closure member 1 so that the defect aperture D is located at the central portion of the closure member 1 when the defect aperture D is closed.

The closure member 1 is an easily foldable flat member and is preferably composed of the closure membrane 11 made of fabrics or nonwoven fabrics of bio-compatible materials, and the frame 12 made of a shape-memory alloy with a shape recovery temperature of 30 to 37° C. and arranged on the peripheral portion of the closure membrane 11. Although the closure member 1 may take any configuration, it is preferred for the closure member 1 to have a flat configuration which is easy to fold and analogous to a shape of the defect aperture D (generally, in a circle), such as a circular, hexagon, octagon and the like. However, the closure member 1 is never limited to these shapes. It is sufficient for the closure member 1 to have a size large enough to close the defect aperture D. In order to assure the closure of the defect aperture D, it is preferred to use the closure member 1 with a size of 1.5 to 2 times the defect aperture D.

Further, the closure member 1 may be provided with a hole 4 to make it easy to hold the closure member with the holding means of the catheter assembly mentioned below.

As the biocompatible material for closure membrane 11, there may be used polyesters such as polyethylene terephthalate; polyolefins such as polyethylene and polypropylene; polyamides such as nylon 6 and nylon 66; fluoroplastics such as polytetrafluoroethylene and polyvinylidene fluoride, chlorine-containing resins such as polyvinyl chloride and polyvinylidene chloride; polyurethane; semisynthetic resins such as cellulose plastics; natural fibers; or the like. These materials may be used in the form of fabrics, nonwoven fabrics, films, porous sheets, or their composites.

The frame 12 is made of a shape-memory alloy having a shape recovery temperature of 30 to 37° C. in the form of a line or wire. Preferred shape-memory alloys generally include Ni—Ti alloys, Cu—Zn—Al alloys, Cu—Al—Ni alloys and the like.

The fixing member 2 for fixing the closure member 1 to the tissue surrounding the defect aperture D is a member to be located on one side of the tissue surrounding the defect aperture D to sandwich the tissue between the fixing member 2 and the closure member 1 located on the opposite side of the tissue surrounding the defect aperture D. The fixing member 2 is made of a shape-memory alloy similar to that of the frame 12 composed of a base 21 and plural arms 22 (generally, two to four elements) extending radially from the base 21 in one plane. The fixing member 2 is fixed to the connecting member 3 so that the arms 22 are approximately parallel to the plane of the closure member 1. The connecting member 3 may be united with the fixing member 2 by suitable connecting means such as welding. In this case, the connected portion between the connecting member 3 and the fixing member 2 is preferably covered with and fixed by a covering member 31 so as to prevent the fixing member 2 from reversing its course.

The connecting member 3 is generally made of the same shape-memory alloy as that used for the frame 11 and fixing member 2 in the form of a slender linear member, and fixed at its one end to the closure member 1 and at the opposite end to the fixing member 2 to hold them in close proximity one another. In order to hold the fixing member 2 substantially parallel to the plane of the closure member 1, the connecting member 3 is arranged approximately parallel to the plane of the closure member 1.

In use, the connecting member 3 is folded first together with the closure member 1 and the fixing member 2 folded in the longitudinal axis of a sheath 6 mentioned below, and then inserted into the sheath 6 of a catheter assembly A shown in FIGS. 4 and 5. During passage of the closure device through the sheath 6, the frame 12, fixing member 2 and connecting member 3 are heated to their recovery temperature by the blood, but they are kept in the folded condition by the sheath as shown in FIG. 5. When the frame 12, arms 22 and connecting member 3 are pushed out of the sheath 6, they are allowed to recover respective original shapes so that the tissue surrounding the defect aperture D is sandwiched between the closure member 1 and fixing member 2.

Next an explanation will be made of the catheter assembly A of the present invention.

Figure 4:
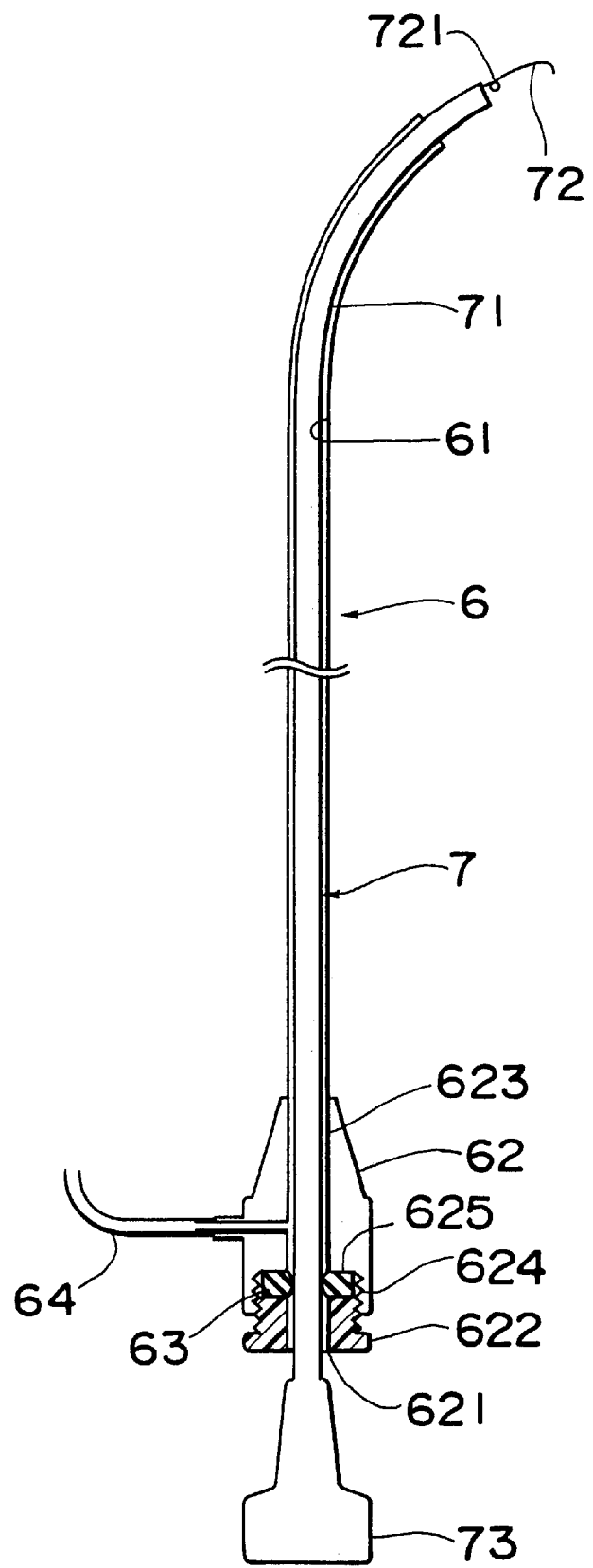
FIG. 4 is a vertical section view illustrating one embodiment of a catheter assembly of the present invention.
Figure 5:
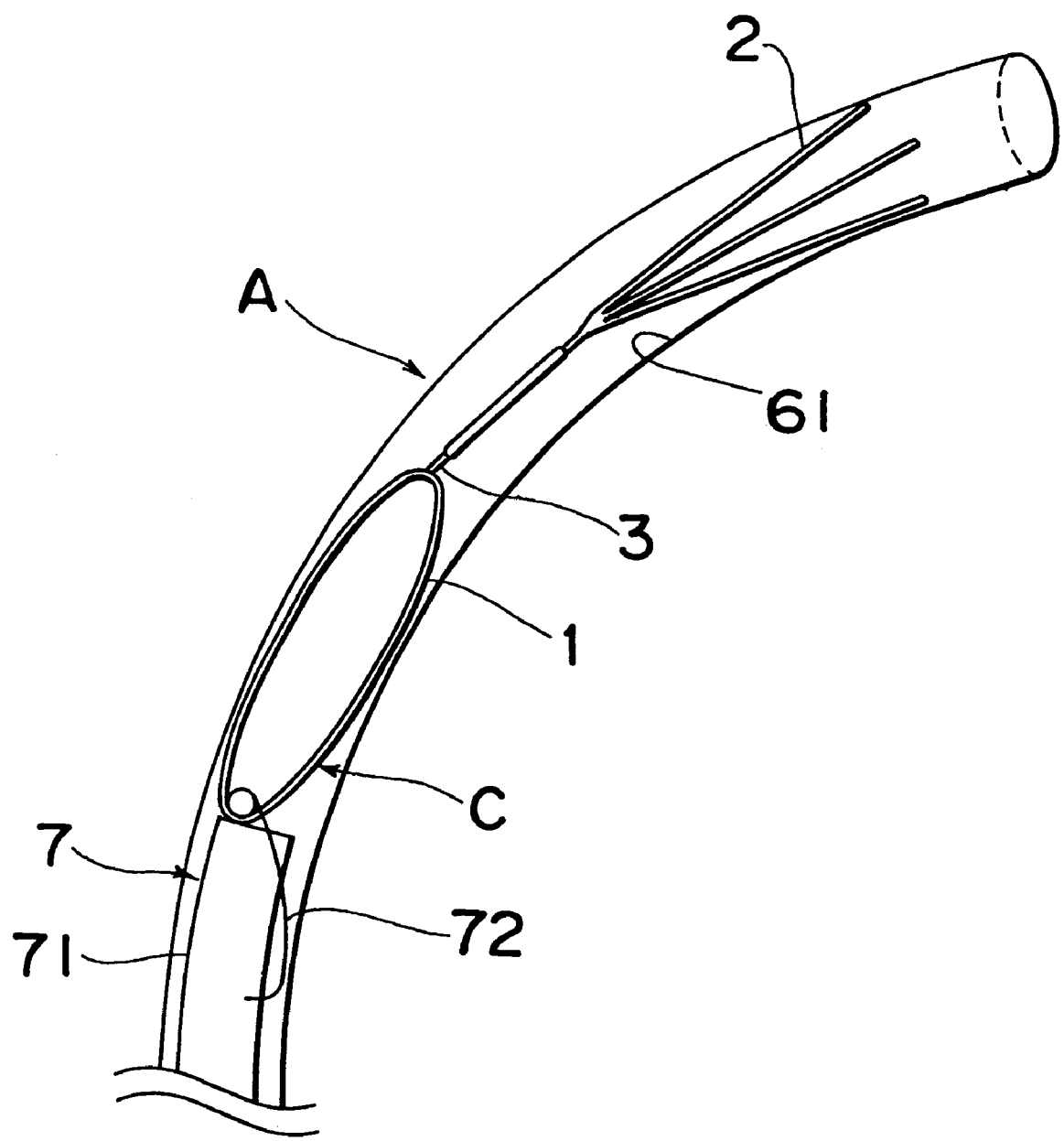
FIG. 5 is a view illustrating the closure device of FIG. 1 put in the catheter assembly shown in FIG. 4.

As shown in FIG. 4, the catheter assembly A of the present invention comprises a sheath 6 and an operating rod 7 for introducing the aforesaid closure device C into the operation site through the sheath 6 to close the defect aperture D with the closure device.

The sheath 6 is a tubular member opened at both ends thereof and has a lumen 61 for holding the folded closure device C therein and for movably holding the operating rod 7. The sheath 6 is provided at its proximal end with a connector 62 having a port 621 for insertion of the operating rod 7, and a stepped through-hole composed of a small-sized portion 623 and a large-sized portion 624 provided coaxially with the small-sized portion 623.

The connector 62 is provided with hemostatic means (e.g., a hemostatic valve) for preventing the blood from leaking during the operations, and a lateral tube 64 for infusion of heparinized physiological saline to prevent coagulation of blood during the operations. The hemostatic means used in this embodiment is composed of a gasket or packing 63 having a through-hole provided in a central part thereof. The packing 63 is set in the large-sized portion 624 and forced against stepped portion 625 of the connector 62 by a bolting member 622 having a through-hole at the central portion thereof.

As a material for the sheath 6, there may be used any one of the materials selected from the group consisting of fluoroplastics such as polytetrafluoroethylene; synthetic resins such as polypropylene and polyethylene, polyesters, polyurethane; and meshed or coiled stainless steels (e.g., SUS 304).

The operating rod 7 is comprised of a rod portion 71, holding means 72 provided at a distal end of the rod portion 71 for releasably holding the closure device C, and a handle 73 for manipulating the operating rod 7 by hand. By manipulating the operating rod, the folded closure device C held by the holding means 72 is inserted into the sheath 6 and then pushed out of the opposite end of the sheath 6.

The holding means 72 is preferably made of an easily flexible linear member extending in the axial direction of the operating rod 7. In this case, a material for the rod portion 71 may be the same material as those used for the sheath 6. As a material for the holding means 72, it is preferred to use an easily flexible elastic material such as, for example, metals such as stainless steels and brasses; flexible plastics such as polypropylene and polyester; super elastic alloys and the like. Preferably, as shown in FIG. 4, the holding means 72 is turned at its proximal portion 721 to form an annular portion that makes it easy to inflect the holding means.

The holding means 72 is turned to hold the closure device C and then inserted into the sheath 6. When the closure device C is pushed out of the sheath 6 by operating the operating rod 7, the holding means 72 is returned to its original shape extending in the axial direction of the operating rod 7 since the holding means 72 is made of an elastic material. Thus, the closure device C is released from the holding means 72.

Next, the use of the catheter assembly A of the present invention will be explained with reference to FIGS. 5 to 8 which show a series of procedures in percutaneous closure treatment employing the closure device and catheter assembly of the present invention.

First of all, the holding means 72 of the operating rod 7 is passed through a part of the closure membrane 11 adjacent to the frame 12 of the closure device C. Then, the closure device C is folded as shown in FIG. 5 (the fixing member 2 and the connecting member 3 are inflected in the longitudinal direction) and then insert into the sheath 6. In this case, the holding means 72 is inserted into the sheath 6 under the condition of being inflected in the direction of the handle 73 to hold the frame 12 of the closure device C.

Next, the catheter assembly A is inserted into an elongated sheath (not illustrated in the figures) previously introduced in a right atrium through a femoral vein of a right leg, to introduce the distal end of the sheath 6 into the right atrium.

Figure 6:
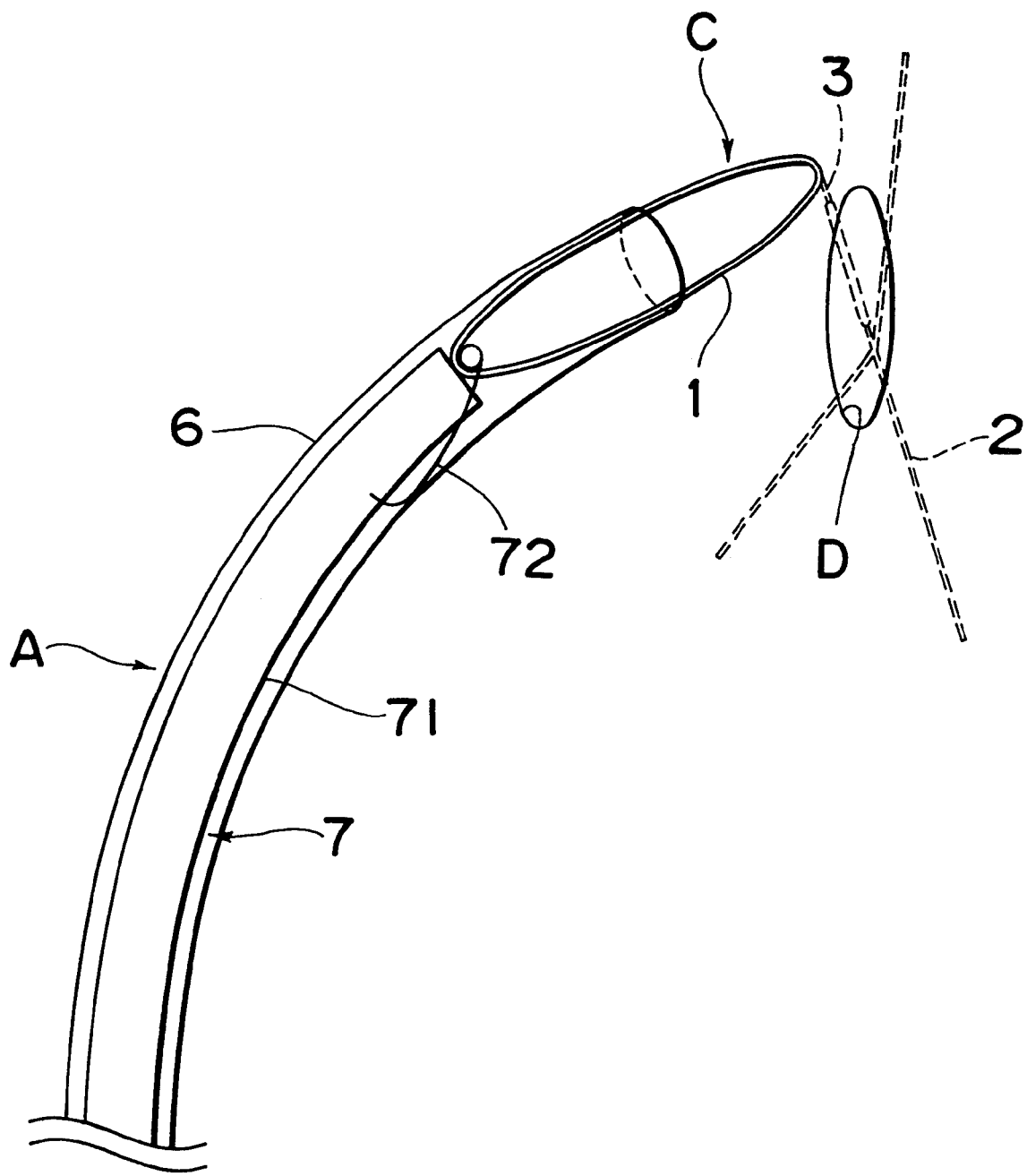
FIG. 6 is an illustration of a percutaneous closure treatment employing the closure device and catheter assembly of the present invention.

After the distal end of the catheter assembly A is protruded from the defect aperture D of the interatrial septum into the left atrium through, the fixing member 2 of the closure device C is pushed out into the left atrium by pushing the operating rod 7. Simultaneously therewith, the fixing member 2 recovers its shape and returns to its original state parallel to the closure member 1, so that the fixing member 2 becomes impossible to pass through the defect aperture D (FIG. 6).

The catheter assembly A is then pulled backward so that its distal end is located in the right atrium. By further pushing the operating rod 7 into the sheath 6, the closure member 1 of the closure device C is pushed out of the sheath 6 in the right atrium and then recovers its unfolded original shape as shown in FIG. 7. The operating rod 7 is further pushed into the sheath 6 (If necessary, with the sheath 6 being pulled back.) to protrude the holding means 72 from the sheath 6. As soon as the holding means 72 is wholly protruded from the sheath 6, it returns to its original shape, i.e., the shape extending in the axial direction of the rod portion 71, thereby disengaging the closure device C. Simultaneously therewith, the recovered closure member 1 is pulled toward the fixing member 2 by elasticity of the frame 12 and connecting member 3 so that the tissue surrounding the defect aperture D is sandwiched between the closure member 1 and the fixing member 2 to close the defect aperture D as shown in FIG. 8. Thus, the operation is finished.

As will be understood from the above description, a defect aperture is closed easily and infallibly through the closure device and catheter assembly for transcatheter operations of the present invention. In addition, the adhesion of thrombus to a closure device, a problem with the use of a closure device of the prior art, can be kept down to minimum therethrough. Also, the closure device can be easily withdrawn from the site even if disembarrassment or dislodgement of the closure device had taken place.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A easily foldable closure device for transcatheter operations, comprising:
   a flat closure member including a closure membrane made of a fabric or a non-woven fabric of a bio-compatible material, and a frame for bordering a periphery of said closure member, said frame being made of a shape-memory alloy with a shape recovery temperature of 30 to 37° C.;
   a fixing member for fixing said closure member to a tissue surrounding a defect aperture, said fixing member being approximately parallel to one plane of said closure member and adapted to be located on one side of said defect aperture so that said tissue is sandwiched between said fixing member and said closure member located on the opposite side of said defect aperture, said fixing member being made of a shape-memory alloy with a shape recovery temperature of 30 to 37° C.; and
   a connecting member fixed at one end to said fixing member and at the other end to the above-mentioned frame of said closure member for holding said closure member and fixing member in close proximity to one another, said connecting member being made of a shape-memory alloy with a shape recovery temperature of 30 to 37° C.

2. The closure device according to claim 1, wherein the frame of the closure member is united with said fixing member and said connecting member.

3. The closure device according to claim 2, wherein a connected portion of said fixing member and said connecting member is covered with a tubular covering member.

4. The closure device according to any one of claims 1 to 3, wherein a base of the fixing member is fixed to the closure membrane of the closure member with a thread for centering the closure member on a defect aperture.

5. The closure device according to any one of claims 1 to 3, wherein the closure member is provided with a hole.

6. A catheter assembly comprising;
   a closure device for transcatheter apertures having:
   a flat closure member including a closure membrane made of a fabric or a non-woven fabric of a bio-compatible material, and a frame for bordering a periphery of said closure membrane, said frame being made of a shape-memory alloy with a shape recovery temperature of 30 to 37° C.;
   a fixing member for fixing said closure member to a tissue surrounding a defect aperture, said fixing member being approximately parallel to one plane of said closure member and adapted to be located on one side of said defect aperture so that said tissue is sandwiched between said fixing member and said closure member located on the opposite side of said defect aperture, said fixing member being made of a shape-memory alloy with a shape recovery temperature of 30 to 37° C.; and
   a connecting member fixed at one end to said fixing member and at the other end to the above-mentioned frame of said closure member for holding said closure member and fixing member in close proximity to one another, said connecting member being made of a shape-memory alloy with a shape recovery temperature of 30 to 37° C.;
   a sheath having opening at both ends and being able to accommodate the folded closure device; and,
   an operating rod provided at a distal end thereof with holding means for releasably holding said closure device, said operating rod being insertable into said sheath from one end thereof under conditions of holding said closure device and being able to unsheathe the closure device through the opposite end of said sheath.

7. The catheter assembly according to claim 6, wherein said holding means is made of an easily flexible linear member extending from the distal end of the operating rod in the axial direction thereof.

* * * * *